US006399798B2

(12) United States Patent
Gschneidner et al.

(10) Patent No.: US 6,399,798 B2
(45) Date of Patent: Jun. 4, 2002

(54) METHOD OF PREPARING ALKYLATED SALICYLAMIDES

(75) Inventors: David Gschneidner; Joseph N. Bernadino, both of Stamford; William E. Bay, Ridgefield, all of CT (US)

(73) Assignee: Emisphere Technologies, Inc., Tarrytown, NY (US)

(*) Notice: Subject to any disclaimer, the term of this patent is extended or adjusted under 35 U.S.C. 154(b) by 0 days.

(21) Appl. No.: 09/922,961

(22) Filed: Aug. 3, 2001

Related U.S. Application Data

(63) Continuation of application No. PCT/US00/03189, filed on Feb. 4, 2000.
(60) Provisional application No. 60/119,207, filed on Feb. 5, 1999, provisional application No. 60/127,754, filed on Apr. 5, 1999, and provisional application No. 60/173,989, filed on Dec. 30, 1999.

(51) Int. Cl.$^7$ ...................... C07C 233/65; C07D 265/26
(52) U.S. Cl. ............................. 554/35; 554/61; 554/62; 554/63; 554/67; 544/94; 562/445; 562/450
(58) Field of Search ............................. 554/63, 35, 61, 554/62, 67; 544/94; 562/444, 450

(56) References Cited

U.S. PATENT DOCUMENTS

| | | | |
|---|---|---|---|
| 2,862,918 A | 12/1958 | Meyer et al. | 530/378 |
| 3,933,873 A | 1/1976 | Love | 554/114 |
| 4,289,759 A | 9/1981 | Heavner | 514/11 |
| 4,757,066 A | 7/1988 | Shiokari | 514/210 |
| 4,835,312 A | 5/1989 | Itoh | 564/205 |
| 5,278,148 A | 1/1994 | Branca | 514/19 |
| 5,310,535 A | 5/1994 | Kruper, Jr. | 424/1.53 |
| 5,650,386 A | 7/1997 | Leoen-Bay et al. | 514/2 |
| 5,773,647 A | 6/1998 | Leone-Bay | 562/444 |
| 5,962,710 A | 10/1999 | Gschneidner | 554/112 |

FOREIGN PATENT DOCUMENTS

| | | |
|---|---|---|
| WO | WO97/10197 | 3/1997 |
| WO | WO98/34632 | 9/1999 |
| WO | WO01/70219 | 9/2001 |

OTHER PUBLICATIONS

Picciola G.: "Sintesi Di Acidi Chiazolinioici E Benzossazinonici E Studio Delle Loro Proprieta Antiniammatorie" IT, Societa Chimica Italiana Pavia vol. 31, No. 9 pp. 655–664 and English Translation, 1976.

Johansen, Marianne, et al. "The Kinetics of decompn. Of various N–Mannich bases of salicylamide" Int. J. Pharm. (1980), 7(2): 119–27 (1980).

Leone–Bay, A. "4–[4–[(2–Hydroxybenzoyl)amino]phenyl] butyric acid as a novel oral delivery agent for recombinant human growth hormone"; Journal of Medicinal Chemistry vol. 39, 2571–2578 (1996).

Leone–Bay, A. "4–[4–[(2–Hydroxybenzoyl)amino]phenyl] butyric acid as a novel oral delivery agent for recombianant human growth hormone"; Journal of Medicinal Chemistry vol. 39, 2571–2578 (1996).

Leone–Bay, A. "N–Acylated alpha–amino acids as novel oral delivery agents for proteins"; Journal of Medicinal Chemistry vol. 38, 4263–4269 (1995).

Ho Koc–Kan; et al. "A Practical Synthesis of ω–aminoalkanoic acid derivatives form Cycloalkanoes" Synthetic Communication, vol. 26, No. 14: 2641–2649 (1996).

Leone–Bay, Andrea; Ho, Koc–Kan; Agarwal, Rajesh; Baughman, Robert A.; Chaudhary,Kiran; DeMorin, Frenel; Genoble, Lise; McInnes, Campbell; Lercara, Christine; Milstein, Sam; O'Toole, Doris.

Sarubbi, Donald; Variano, Bruce; and Paton, Duncan R.;"Synthesis and Evaluaiton of Compounds That Facilitate the Gastrointestinal Absorption of Heparin"; Journal of Medicinal Chemistry (1998) 41: 1163–1171.

Gurrieri and Siracusa: "Thermal Condensation of Some alpha–aminoacids with Phatalic Acid" Thermochimica Acta, 7 (1973) 231–239.

Amino Yusuke et al. Chem Pharm Bull 36 pgs. 4426–4434 (1988).

Trapani, Giuseppe; Reho, Antonia; Latrofa, Andrea: Trimethylamine–Borane as Useful Reagent in the N–Alkylatin of Amines by Carboxylic Acids:: Synthesis International Journal of Methods of Synthetic Organic Chemistry 12:1013 (Dec. 1983).

Tani, Junichi; Oine, Toyonari; Inoue, Ichizo: : Synthesis International Journal of Methods of Synthetic Organic Chemistry, 11:714(Nov. 1975).

*Primary Examiner*—Shailendra Kumar
(74) *Attorney, Agent, or Firm*—Darby & Darby

(57) ABSTRACT

The present invention relates to a method of preparing an alkylated salicylamide from a protected and activated salicylamide (hereinafter referred to as a "protected/activated salicylamide"). The method comprises the steps of (a) alkylating the protected/activated salicylamide with an alkylating agent to form a protected/activated alkylated salicylamide, and (b) deprotecting and deactivating the protected/activated alkylated salicylamide, simultaneously or in any order, to form the alkylated salicylamide. The alkylated salicylamides prepared by this method are suitable for use in compositions for delivering active agents via oral or other routes of administration to animals.

20 Claims, No Drawings

METHOD OF PREPARING ALKYLATED SALICYLAMIDES

This is a continuation of International Application Serial No. PCT/US00/03189, filed Feb. 4, 2000 and claims the benefit of U.S. Provisional Application No. 60/119,207, filed Feb. 5, 1999; U.S. Provisional Application No. 60/127,754, filed Apr. 5, 1999; and U.S. Provisional Application No. 60/173,989, filed Dec. 30, 1999, all of which are hereby incorporated by reference.

FIELD OF THE INVENTION

The present invention relates to a method of preparing alkylated salicylamides from salicylamides. The alkylated salicylamides prepared by this method are suitable for use in compositions for delivering active agents via oral or other routes of administration to animals.

BACKGROUND OF THE INVENTION

Carsalam (2H-1,3-benzoxazine-2,4(3H)-dionc) is known in the art as an analgesic (see Merck Index, 12th edition, #1915).

Alkylated salicylamides, such as those disclosed in U.S. Pat. No. 5,650,386, have been found to be highly effective as delivery agents for active agents, particularly for oral administration of active agents. Typically, these alkylated salicylamides are prepared by modifying an amino acid or an ester thereof. For example, these alkylated salicylamides may be prepared by acylation of an amino acid or an ester thereof with agents having a leaving group, such as a halogen, carbonyl group, or sulfonyl group, and an appropriate radical to yield the desired modification in the final product. See, for example, U.S. Pat. No. 5,650,386.

Alternate methods of producing alkylated salicylamides would be useful, especially where raw materials are expensive, yields are low, and/or reaction conditions are difficult.

Therefore, there is a need for simpler and less expensive methods of preparing alkylated salicylamides.

SUMMARY OF THE INVENTION

The present invention relates to a method of preparing an alkylated salicylamides from a protected and activated salicylamide (hereinafter referred to as a "protected/activated salicyamide"). The method comprises the steps of (a) alkylating the protected/activated salicylamide with an alkylating agent to form a protected/activated alkylated salicylamide and (b) deprotecting and deactivating the protected/activated alkylated salicylamide, simultaneously or in any order, to form the alkylated salicylamide. The alkylated salicylamides prepared by this method are suitable for use in compositions for delivering active agents via oral or other routes of administration to animals.

DETAILED DESCRIPTION OF THE INVENTION

The term "protected salicylamide" is defined herein as a salicylamide where the hydroxy moiety of the salicyl group has been protected to prevent reaction of the hydroxy moiety. The term "activated salicylamide" is defined herein as a salicylamide where the nitrogen atom of the amide group has been activated so that the nitrogen atom is in a more reactive condition, i.e., more prone to reaction.

Suitable protected/activated salicylamides include, but are not limited to, compounds having the formula

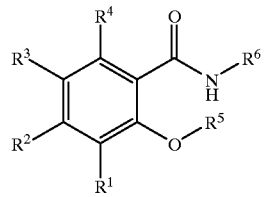

where $R^1$, $R^2$, $R^3$, and $R^4$ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)CH$_3$; —SO$_3$H; nitrile; or —NR$^9$R$^{10}$;

$R^9$ and $R^{10}$ are independently hydrogen, $C_1$–$C_4$ alkyl, or oxygen;

$R^5$ is a protecting group;

$R^6$ is an activating group; or $R^5$ and $R^6$ are combined to form a cyclic group, i.e., $R^5$ and $R^6$ form a single group that forms a heterocycle with the oxygen atom and nitrogen atom of the amide moiety.

Preferred halogens for $R^1$, $R^2$, $R^3$, and $R^4$ are chlorine, bromine, and fluorine. Preferred alkoxy groups for $R^1$, $R^2$, $R^3$, and $R^4$ include, but are not limited to, methoxy and ethoxy.

Suitable protecting groups include, but are not limited to, —C(O)CH$_3$; —C(O)F$_3$; —S(O)$_2$CH$_3$; —S(O)$_2$CF$_3$; benzyl; silyl; tetrahydropyranyl; and methylenealkoxy, such as methylenemethoxy and methyleneethoxy. Suitable activating groups include, but are not limited to, —C(O)CH$_3$; —C(O)CF$_3$; —S(O)$_2$CH$_3$; and —S(O)$_2$CF$_3$. Preferably, $R^5$ and $R^6$ are combined to form a cyclic group which protects the hydroxy moiety and activates the nitrogen atom of the amide moiety. More preferably, combined $R^5$ and $R^6$ are —C(O)— or —S(O)$_2$—.

Preferred protected/activated salicylamides include, but are not limited to, carsalam and derivatives thereof having the formula

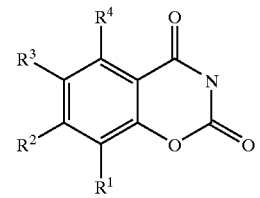

where $R^1$, $R^2$, $R^3$, and $R^4$ are defined as above.

Carsalam has the formula

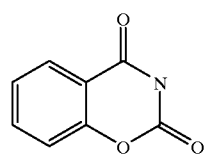

Carsalam may be prepared by methods known in the art, such as those described in Shapiro et al., *JACS*, 79:2811 (1957), and D. N. Dhar, A. K. Bag, *Indian J. Chem.*, 21B:266 (1982). The aforementioned carsalam derivatives may be prepared by methods known for preparing carsalam substituting appropriate starting materials. These carsalam derivatives may also be prepared by adding the appropriate substituents to carsalam by methods known in the art.

One method of preparing the protected/activated salicylamide of the present invention comprises protecting the hydroxy moiety of a salicylamide and activating the amide moiety of the salicylamide. The protecting and activating steps may be performed in any order, but are preferably performed simultaneously. For example, the protecting step may be performed before performing the activating step.

Suitable (unprotected and unactivated) salicylamides include, but are not limited to, those having the formula

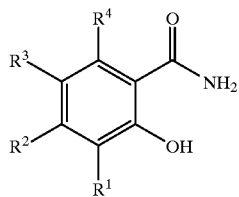

where $R^1$, $R^2$, $R^3$, and $R^4$ are defined as above.

The hydroxy moiety of the salicylamide may be protected by methods known in the art. For example, the hydroxy moiety may be protected by reacting the salicylamide with a protecting agent, such as an activated halide. The resulting salicylamide has a protecting group attached to the oxygen atom of the hydroxy moiety. Examples of activated halides include, but are not limited to, acyl halides; silyl halides, such as silyl chlorides; benzyl halides; and methylene alkoxy halides, such as methylene methoxy halides and methylene ethoxy halides. Preferably, the reaction with an activated halide is performed in the presence of a base, such as potassium carbonate, triethylamine, or pyridine.

Another example of a protecting agent is an activated ether. Examples of activated ethers include, but are not limited to, dihydropyranyl ether. Preferably, the activated ether is reacted with the salicylamide under acid catalysis conditions, such as with sulfuric acid, paratoluene sulfonic acid, or camphor sulfonic acid in methylene chloride, tetrahydrofuran, or toluene.

The amide moiety of the salicylamide may be activated by methods known in the art. For example, the amide moiety may be activated by reacting the salicylamide with an activating agent, such as an acyl halide, acyl anhydride, sulfonyl halide, or sulfonyl anhydride. The resulting salicylamide has an activating group attached to the nitrogen atom of the amide moiety. Suitable acyl halides include, but are not limited to, those described above for protecting the hydroxy moiety of the salicylamide. Preferably, the activating agent is reacted with the salicylamide in the presence of a base, such as potassium carbonate, triethylamine, or pyridine.

The protecting and activating groups may be the same or different. The protecting and activating groups may be separate moieties (each attached to one of the hydroxy or amide moieties) or a single moiety (attached to both the hydroxy and amide moieties).

In the preparation of carsalam and the aforementioned derivatives thereof, the protecting and activating steps are typically performed simultaneously and the protecting and activating groups are a single group attached to both the hydroxy and amide moieties. One method of preparing carsalam and the derivatives thereof is by reacting the corresponding (unprotected and unactivated) salicylamide with an alkyl chloroformate, such as ethyl chloroformate; a phenyl chloroformate; or an imidazole alkoxy carbonyl.

The protected/activated salicylamide may be alkylated by the methods known in the art for alkylating phthalimide to form a primary amine. Sec, for example, Gibson and Bradshaw, *Angewandte Chemie*, International Edition in English, 7:919–930 (1968). The protected/activated salicylamide is substituted for the phthalimide in these methods.

The protected/activated salicylamide may also be alkylated by reacting the protected/activated salicylamide with an alkylating agent. The alkylating agent reacts with the nitrogen atom of the amide moiety of the salicylamide. The alkylating agent may be any known in the art, such as compounds of the formula

where $R^7$ is a linear or branched, $C_1$–$C_{20}$ alkylene, alkenylene, or alkynylene;

$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteroaryl, or vinyl;

$R^7$ is optionally interrupted with aryl, heteroaryl, vinyl, oxygen, nitrogen, or sulfur;

$R^8$ is carboxyl or a salt thereof, carboxylate, nitrile, halogen, ester, amine or salt thereof, alcohol, or thiol; and X is a suitable leaving group. Suitable leaving groups include, but are not limited to, halogens, such as chlorine and bromine, and alcohols. Two preferred leaving groups are chlorine and bromine.

$R^7$ may be substituted with an alkoxy moiety, such as methoxy or ethoxy. Preferably, $R^7$ is —$(CH_2)_n$— where n is an integer from about 1 to about 12, more preferably from about 7 to about 9, and most preferably about 7.

$R^8$ is preferably a carboxyl or a salt thereof. Salts include, but are not limited to, organic and inorganic salts, for example, alkali-metal salts, such as sodium, potassium and lithium; alkaline-earth metal salts, such as magnesium, calcium or barium; ammonium salts; basic amino acids, such as lysine and arginine; and organic aminos, such as dimethylamine and pyridine. More preferably, $R^8$ is a sodium salt of carboxyl.

In a preferred embodiment, $R^1$, $R^2$, $R^3$, and $R^4$ of the protected/activated salicylamide are hydrogen and $R^7$ of the alkylating agent is —$(CH_2)_7$— or —$(CH_2)_9$—. According to another preferred embodiment, $R^1$, $R^2$, and $R^4$ of the protected/activated salicylamide are hydrogen, $R^3$ is chlorine, and $R^7$ of the alkylating agent is —$(CH_2)_3$— or —$(CH_2)_7$.

The reaction between the alkylating agent and the protected/activated salicylamide is preferably carried out in the presence of a slight molar excess of protected/activated salicylamide relative to alkylating agent. Generally, the molar ratio of protected/activated salicylamide to alkylating agent ranges from about 1:1 to about 1:0.5, preferably from about 1:0.8 to about 1:0.99, and most preferably about 1:0.95.

The alkylating reaction is preferably performed in the presence of a suitable base, such as pyridine, triethylamine, diisopropylethylamine, sodium or potassium bicarbonate, sodium or potassium carbonate, or any combination of any of the foregoing. Preferably, the base is sodium carbonate. The reaction may be carried out in solvents, such as dimethylacetamide and dimethylformamide.

The alkylating reaction is generally performed at a temperature of from about 20 to about 100° C. The reaction is preferably performed at a temperature of from about 50 to about 80° C. and most preferably at about 70° C. The reaction is generally performed for a time sufficient to ensure the complete reaction of the protected/activated salicylamide. The reaction duration varies depending on the starting materials. Generally, the reaction is allowed to run for a time sufficient so that at least about 90% and preferably 99% of the limiting, reagent, i.e., the alkylating agent, has been consumed, but is stopped before significant side reaction product build up. This reduces or eliminates the need for purification of the final product. Preferably, it is performed for from about 2 to about 18 hours, more preferably from about 3 to about 5 hours, and most preferably about 4 hours.

The alkylation reaction may be performed with alcohols under Mitsunobu conditions. See Mitsunobu, W. and Sano, J., *J. Amer. Chem. Soc.*, 94:674 (1972). Such alkylation reactions are performed in the presence of triphenylphosphene ($PPh_3$) and dialkyl azodicarboxylates, such as diisopropyl azodicarboxylate (DIAD). The products of this reaction may be hydrolyzed to the corresponding alkylated salicylamides.

The protected/activated alkylated salicylamide is then deprotected and deactivated to yield the alkylated salicylamide. Typically, this step entails the removal of the protecting and activating groups from the salicylamide. The protecting and activating groups may be removed by acidic, basic and/or neutral hydrolysis as known in the art.

Phenolic protecting groups, except for acylated phenolic protecting groups, may be removed by acidic hydrolysis. Acidic hydrolysis may be performed, for example, with aqueous hydrochloric acid or aqueous trifluoroacetic acid. Acylated phenolic protecting groups generally are removed by basic hydrolysis.

The activating groups may be removed from the amide moiety by basic hydrolysis. Basic hydrolysis may be performed, for example, with aqueous sodium carbonate or aqueous sodium hydroxide.

Neutral hydrolysis may be performed, for example, with super-heated water at a temperature of from about 100 to about 250° C.

The deprotecting and deactivating step may be performed at a temperature of from about 20 to about 100° C. and preferably from about 90 to about 100° C.

Suitable solvents for the protected/activated alkylated salicylamide in the deprotecting and deactivating step include, but are not limited to, water, ethanol, and any combination of any of the foregoing.

When the protected/activated salicylamide is carsalam or a derivative thereof, the alkylated salicylamide may be deprotected and deactivated by hydrolysis. This causes the bonds between the carbonyl group and the adjacent oxygen atoms to cleave, thereby deprotecting the hydroxyl moiety. Hydrolysis may be carried out under conditions known in the art. For example, basic hydrolysis may be performed with an alcoholic solvent, such as ethanol.

After hydrolysis of the carsalam or carsalam derivative, the activated salicylamide may be deactivated by methods known in the art. For example, hydrochloric acid may be added to the activated alkylated salicylamide until the pH of the reaction mixture is less than about 4. This causes the bond between the carbonyl moiety and the nitrogen atom of the amide moiety of the salicylamide to cleave and release carbon dioxide.

Optionally, the alkylated salicylamide may be further reacted to modify the end group of the alkylating moiety, i.e., $R^8$. For example, the end group —CN or —C(O)O—$CH_2$—$CH_3$ may be modified to —COOH or a salt thereof. This may be accomplished by methods known in the art, such as acidic and basic hydrolysis.

The present method may be used to prepare alkylated salicylamides having the formula

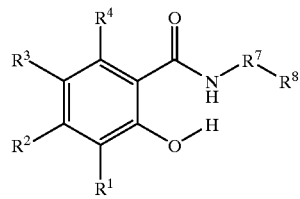

where $R^1$, $R^2$, $R^3$, $R^4$, $R^7$, and $R^8$ are defined as above.

The alkylated salicylamides of the present invention may be purified by recrystallization or fractionation on one or more chromatographic supports. Fractionation may be performed on suitable chromatographic supports, such as silica gel or alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The alkylated salicylamides may also be purified to remove impurities, such as inorganic salts, by extraction with a lower alcohol, such as methanol, butanol, or isopropanol.

The method of the present invention uses readily available and inexpensive starting materials and provides a cost-effective method for preparing and isolating alkylated salicylamides. The method is simple to perform and is amenable to industrial scale-up for commercial production.

The invention will now be illustrated in the following non-limiting examples which are illustrative of the invention but are not intended to limit the scope of the invention.

DESCRIPTION OF THE PREFERRED EMBODIMENTS

EXAMPLE 1

Preparation of 2H-1,3-Benzoxazine-2,4(3H)-dione (Carsalam)

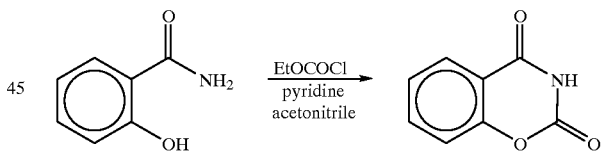

Following the method of Shapiro et al., *JACS*, 79:2811 (1957), salicylamide (59.0 g, 0.43 mol, 1.0 eq), pyridine (150 mL) and acetonitrile (125 mL) were placed in a 500 mL three-neck flask equipped with a magnetic stir bar, a thermometer, and an addition funnel. After cooling to about 5° C. in a salt ice bath, ethyl chloroformate (45.2 mL, 0.47 mol, 1.1 eq) was added dropwise over 25 minutes so that the reaction temperature did not exceed 10° C. during the addition. The reaction mixture was stirred for 30 minutes at 10° C. The addition funnel was replaced with a Dean-Stark trap and a water-cooled condenser. The mixture was heated to a distillation temperature of about 90° C. Distillation was continued until the internal temperature reached about 124° C. (200 ml. of distillate removed). The temperature was reduced so that the reaction mixture refluxed but did not distill. After one hour at reflux, the reaction mixture was cooled to about 25° C. and poured into water (400 mL). Concentrated aqueous hydrochloric acid (24 mL) was added. A white solid formed, which was collected by filtration, washed with water (200 mL), and dried under vacuum. The 2H-1,3-benzoxazine-2,4(3H)-dione was isolated as a white solid (59.3 g, 85% yield).

EXAMPLE 2

Preparation of 3-(7-Heptylnitrile)-2H-1,3-benzoxazine-2,4(3H)-dione

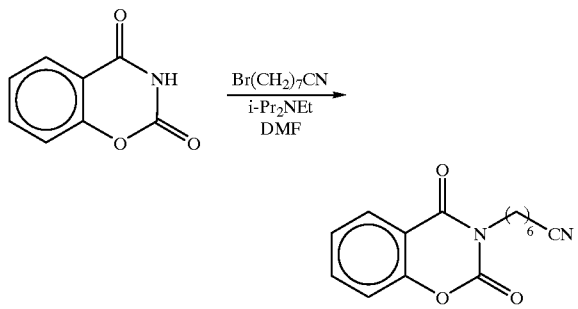

7-Bromoheptanenitrile (20.0 g, 0.105 mol, 1.0 eq), 2H-1,3-benzoxazine-2,4(3H)-dione (18.2 g, 0.112 mol, 1.07 eq) and dimethylformamide (50 mL) were placed in a 250 mL round bottom flask equipped with a magnetic stir bar and a water-cooled condenser. Diisopropylethylamine (20.0 mL, 14.8 g, 0.115 mol, 1.1 eq) was added and the reaction mixture was heated to about 70° C. After 6 hours, HPLC indicated that the reaction was complete. The reaction mixture was cooled to 25° C., poured into ethyl acetate (100 mL), washed with 3% aqueous hydrochloric acid (2×80 ml.), water, and brine (1×80 mL each). The resulting solution was dried over disodium sulfate and concentrated under vacuum to yield 3-(7-heptylnitrile)-2H-1,3-benzoxazine-2,4(3H)-dione (20 g; 77%) as a white solid.

EXAMPLE 3

Preparation of N-(7-(2-hydroxybenzoyl)amino) heptanoic Acid

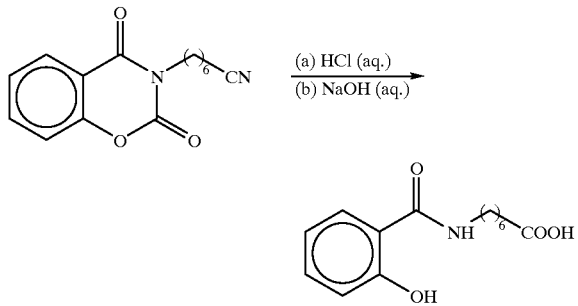

3-(7-heptylnitrile)-2H-1,3-benzoxazine-2,4(3H)-dione (25.22 g, 0.102 mol, 1.0 eq) and concentrated aqueous hydrochloric acid (75 mL, 0.918 mol, 9.0 eq) were placed in a 250 mL round bottom flask equipped with a magnetic stir bar and a water-cooled reflux condenser. The suspension was heated to about 50° C. for 150 minutes and then to 95° C. for 250 minutes, when HPLC indicated that the reaction was complete. The solids formed, were removed by filtration, and dissolved in 2N sodium hydroxide. After stirring overnight, tile solution was acidified with 2% aqueous hydrochloride solution. The resulting precipitate was collected by filtration and recrystallized from 50% methanol/water. N-(7-(2-hydroxybenzoyl)amino)heptanioc acid was isolated as a white solid (16.73 g, 62%) (melting point: 85–89° C.).

EXAMPLE 4

Preparation of Ethyl 3-(10-Decanoate)-2H-1,3-benzoxazine-2,4(3H)-dione

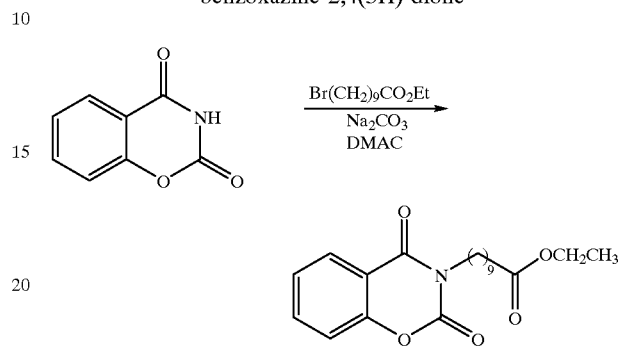

A 1 L, Pyrex glass, jacketed, bottom drain, laboratory reactor was used to perform this experiment. The temperature in the reactor was controlled with a circulating oil heat exchanger attached to the jacket on the reactor. This heat exchanger was capable of both cooling and heating. The reactor was equipped with an overhead turbine blade stirrer, temperature probe, distillation head, distillate condenser, and distillation receiver. The reactor was purged with nitrogen and attached to a vacuum pump with a vacuum controller. The vacuum release valve on the vacuum controller was connected to a nitrogen source in order to keep atmospheric air out of the reactor.

Dry N,N-dimethylacetamide (275 mL) was charged to the reactor and the stirrer started. Sodium carbonate (47.7 g, 0.45 mol, 1.05 eq), ethyl 10-bromo-decanoate (119.4 g, 0.43 mol, 1.0 eq), and 2H-1,3-benzoxazine-2,4(3H)-dione (73.2 g, 0.45 mol, 1.05 eq) were sequentially charged to the reactor in this order at ambient temperature. The vacuum pump was started and the absolute pressure adjusted to 180 mm Hg. The reaction mixture was heated from ambient temperature to about 70° C. over 45 minutes and held at this temperature for six to eight hours. The reaction progress was monitored by gas chromatography and judged to be complete when all of the ethyl 10-bromo-decanoate had been consumed. After completion of the reaction, the reaction mixture temperature was lowered to approximately 40° C. The reaction mixture was drained into a sintered glass filter funnel and vacuum filtered directly into a 2 L round bottom flask. The reactor was rinsed with ethanol (280 mL) and this rinse was used to wash the filter cake. This ethanol wash was allowed to combine with the previous reaction mixture filtrate. The filter funnel was removed from the 2 L round bottom flask. This reaction flask was then equipped with an overhead stirrer, thermometer, water bath, and addition funnel. The addition funnel was charged with deionized water (150 mL). The stirred filtrate was cooled to about 25° C. and the water was added dropwise. Care was taken to make sure that the water dropped directly into the stirred filtrate mixture. The water was not allowed to dribble down the wall of the 2 L round bottom flask. The resulting slurry was cooled to between 5 and 10° C. when the water addition was complete. White solids were recovered by vacuum filtration through a sintered glass filter funnel. The 2 L round bottom flask was then charged with ethanol (175 mL) and the ethanol was cooled with stirring to between 5 and 10° C. The cold ethanol was then used to wash the filter cake. The 2 L round bottom flask was then charged with heptane (225 mL) and the heptane was cooled with stirring to between 5 and 10° C. The cold heptane was then used to wash the filter cake. The filter cake was then sampled and analyzed by gas chromatography. The filter cake was washed with more heptane if ethyl 10-bromo-decanoate was found in the sample. The cake was either used as is in the next step of the reaction sequence or was vacuum dried in a 40° C. oven for storage. The yield of ethyl 3-(10-decanoate)-2H-1,3-benzoxazine-2,4(3H)-dione was about 90%.

EXAMPLE 5

Alternate Preparation of Ethyl 3-(10-Decanoate)-2H-1,3-benzoxazine-2,4(3H)-dione

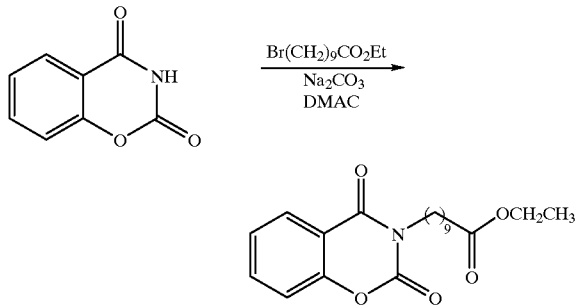

A 1 L, Pyrex glass, jacketed, bottom drain, laboratory reactor was used to perform this experiment. The temperature in the reactor was controlled with a circulating oil heat exchanger attached to the jacket on the reactor. This heat exchanger was capable of both cooling and heating. The reactor was equipped with an overhead turbine blade stirrer, temperature probe, and reflux condenser. The reactor was purged with nitrogen and the reaction was performed under an atmosphere of nitrogen.

Dry N,N-dimethylacetamide (232 mL), 2H-1,3-benzoxazine-2,4(3H)-dione (62.0 g, 0.38 mol, 1.05 eq), and ethyl 10-bromo-decanoate (101.0 g, 0.36 mol, 1.0 eq) were charged to the reactor and the stirrer started. The reaction mixture was heated to about 70° C. over a 45 minute period. The reaction mixture was a nearly clear solution at this time. Sodium carbonate (45.0 g, 0.42 mol, 1.17 eq) was added in portions to the stirred reaction. There was some foaming during the initial part of the sodium carbonate addition. The reaction was held at about 70° C. for four hours after the sodium carbonate addition was complete. The reaction mixture temperature was lowered to approximately 40° C. The reaction mixture was drained into a sintered glass filter funnel and vacuum filtered into a 2 L side arm filter flask. The reactor was rinsed with ethanol (125 mL) and this rinse was used to wash the filter cake. This ethanol wash was allowed to combine with the previous reaction mixture filtrate. The filter flask was placed in an ice bath and the filtrate stirred magnetically. Deionized water (125 mL) was added to the stirred filtrate. The resulting slurry was stirred for 30 minutes while the ice bath remained in place. White solids were recovered by vacuum filtration through a sintered glass filter funnel. The filter cake was washed with heptane (155 mL). The cake was either used as is in the next step of the reaction sequence or was vacuum dried in a 40° C. oven for storage. The yield of ethyl 3-(10-decanoate)-2H-1,3-benzoxazine-2,4(3H)-dione was 90 to 95%.

EXAMPLE 6

Preparation of N-(2-hydroxybenzoyl)-10-amino)-decanoic Acid

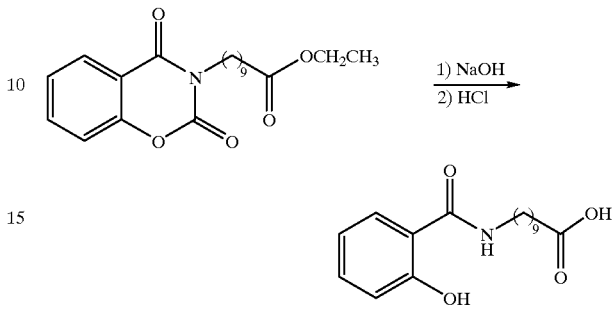

A 1 L stainless steel resin flask was set up with a stainless steel overhead turbine blade stirrer, stainless steel jacketed thermocouple thermometer, reflux condenser, and heating mantle. The reactor was charged with ethyl 3-(10-decanoate)-2H-1,3-benzoxazine-2,4(3H)-dione (200 g, 0.55 mol, 1.0 eq) and 20% (by weight) aqueous sodium hydroxide (443 g, 2.22 mol, 4.0 eq). The stirrer was started and the reaction slurry heated to about 98° C. over a 30 minute period. The reaction mixture was held at this temperature for one to two hours. The reaction mixture became a clear solution after the first hour at about 98° C.

A second reactor was set up with a three liter, round bottom, four neck flask. This reactor was equipped with a thermocouple thermometer, overhead stirrer, reflux condenser, ice bath cooling basin, and addition funnel. This reactor was charged with deionized water (310 mL), 37% (by weight) hydrochloric acid (197 g, 2.00 mol, 3.64 eq), and acetone (295 mL). The hydrolysis mixture in the stainless steel reactor was cooled to about 40° C. and transferred to the addition funnel on the second reactor. The stainless steel reactor was rinsed into the addition funnel with deionized water (50 mL). The hydrolysis mixture was added slowly with stirring to the hydrochloric acid solution. This addition was accompanied by the immediate precipitation of white solids in the acidification mixture. The addition rate was adjusted so that the foaming was controllable. The acidification reaction temperature was kept at approximately 45° C. with ice bath cooling. The pH of the acidification was adjusted to between 4.0 and 4.5 after the addition was complete by the incremental addition of concentrated hydrochloric acid. The ice bath was replaced with a heating mantle and the temperature of the acidified reaction mixture raised to about 65° C. and held at this temperature for 30 minutes. The solids in the acidification mixture formed an emulsion during heating. The reaction mixture was stirred and slowly cooled to ambient temperature to yield a slurry. The solids in this slurry were recovered by vacuum filtration through a sintered glass funnel. The filter cake was washed with deionized water (230 mL). The wet cake was vacuum dried at about 50° C. overnight. The yield of N-(2-hydroxybenzoyl)-10-aminodecanoic acid was 85 to 95%.

EXAMPLE 7

Alternate Preparation of N-(2-hydroxybenzoyl)-10-amino-decanoic Acid

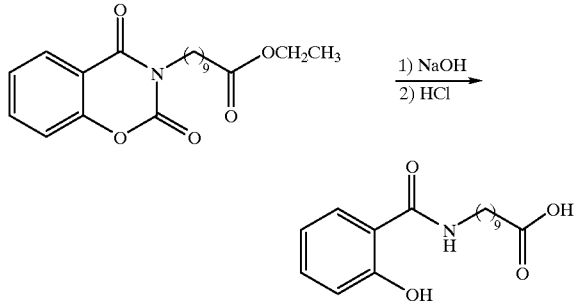

A 1 L stainless steel resin flask was set up with a stainless steel overhead turbine blade stirrer, stainless steel jacketed thermocouple thermometer, reflux condenser, and heating mantle. The reactor was charged with ethyl 3-(10-decanoate)-2H-1,3-benzoxazine-2,4(3H)-dione (200 g, 0.55 mol, 1.0 eq) and 20% (by weight) aqueous sodium hydroxide (443 g, 2.22 mol, 4.0 eq). The stirrer was started and the reaction slurry heated to about 98° C. over a 30 minute period. The reaction mixture was held at this temperature for one to two hours. The reaction mixture became a clear solution after the first hour at about 98° C.

A second reactor was set up with a three liter, round bottom, four neck flask. This reactor was equipped with a thermocouple thermometer, overhead stirrer, reflux condenser, water bath cooling basin, and addition funnel. The second reactor was charged with deionized water (310 mL), 37% (by weight) hydrochloric acid (218.5 g, 2.22 mol, 4.0 eq). The hydrolysis mixture in the stainless steel reactor was cooled to ambient temperature and transferred to the addition funnel on the second reactor. The hydrolysis mixture was added slowly with stirring to the hydrochloric acid solution. This addition was accompanied by the immediate precipitation of white solids in the acidification mixture. The addition rate was adjusted so that the foaming was controllable. This acidification is exothermic and the reaction temperature was allowed to rise to about 45° C. and kept at this temperature with occasional water bath cooling. The pH of the resulting slurry was adjusted with concentrated hydrochloric acid or 2N sodium hydroxide as needed to bring the final pH to between 4.0 and 4.5. The reaction mixture was then heated to about 65° C. and held at this temperature for 30 minutes. The reaction mixture was slowly cooled with stirring to ambient temperature. The solids in this slurry were recovered by vacuum filtration through a sintered glass funnel. The filter cake was washed with deionized water (230 mL). The wet cake was vacuum dried at about 50° C. overnight. The yield of N-(2-hydroxybenzoyl)-10-aminodecanoic acid was 85 to 95%.

EXAMPLE 8

Preparation of Ethyl 3-(8-Octanoate)-2H-1,3-benzoxazine-2,4(3H)-dione

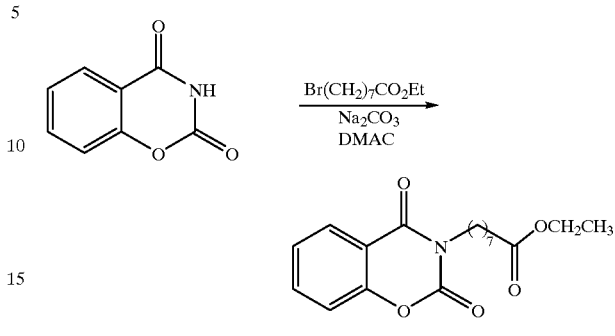

A 1 L, Pyrex glass, jacketed, bottom drain, laboratory reactor was used to perform this experiment. The temperature in the reactor was controlled with a circulating oil heat exchanger attached to the jacket on the reactor. This heat exchanger was capable of both cooling and heating. The reactor was equipped with an overhead turbine blade stirrer, temperature probe, distillation head, distillate condenser, and distillation receiver. The reactor was purged with nitrogen and attached to a vacuum pump with a vacuum controller. The vacuum release valve on the vacuum controller was connected to a nitrogen source in order to keep atmospheric air out of the reactor.

Dry N,N-dimethylacetamide (233 mL) was charged to the reactor and the stirrer started. Sodium carbonate (85.8 g, 0.81 mol, 2.24 eq), ethyl 8-bromo-octanoate (90.7 g, 0.36 mol, 1.0 eq), and 2H-1,3-benzoxazine-2,4(3H)-dione (66.0 g, 0.40 mol, 1.12 eq) were sequentially charged to the reactor in this order at ambient temperature. The vacuum pump was started and the absolute pressure adjusted to 180 mm Hg. The reaction mixture was heated from ambient temperature to about 70° C. over 45 minutes and held at this temperature for six to eight hours. The reaction progress was monitored by gas chromatography and judged to be complete when all of the ethyl 8-bromo-octanoate had been consumed. The reaction mixture temperature was lowered to approximately 40° C. The reaction mixture was drained into a sintered glass filter funnel and vacuum filtered directly into a 2 L round bottom flask. The reactor was rinsed with ethanol (125 mL) and this rinse was used to wash the filter cake. The ethanol wash was allowed to combine with the previous reaction mixture filtrate. The filter funnel was removed from the 2 L round bottom flask. This reaction flask was then equipped with an overhead stirrer, thermometer, water bath, and addition funnel. The addition funnel was charged with deionized water (125 mL). The stirred filtrate was cooled to about 25° C. and the water was added dropwise. Care was taken to make sure that the water dropped directly into the stirred filtrate mixture. The water was not allowed to dribble down the wall of the 2 L round bottom flask. The resulting slurry was cooled to between 5 and 10° C. when the water addition was complete. White solids were recovered by vacuum filtration through a sintered glass filter funnel. The 2 L round bottom flask was charged with ethanol (175 mL) and the ethanol cooled with stirring to between 5 and 10° C. The cold ethanol was then used to wash the filter cake. The 2 L round bottom flask was then charged with heptane (225 mL) and the heptane was cooled with stirring to between 5 and 10° C. The cold heptane was then used to wash the filter cake. The filter cake was then sampled and analyzed by gas chromatography. The filter cake was then washed with more heptane if ethyl 10-bromo-decanoate was found in the sample. The cake was either used as is in the next step of the reaction sequence or was vacuum dried in a 40° C. oven for storage. The yield of ethyl 3-(8-octanoate)-2H-1,3-benzoxazine-2,4(3H)-dione was about 90%.

EXAMPLE 9

Alternate Preparation of Ethyl 3-(8-Octanoate)-2H-1,3-benzoxazine-2,4(3H)-dione

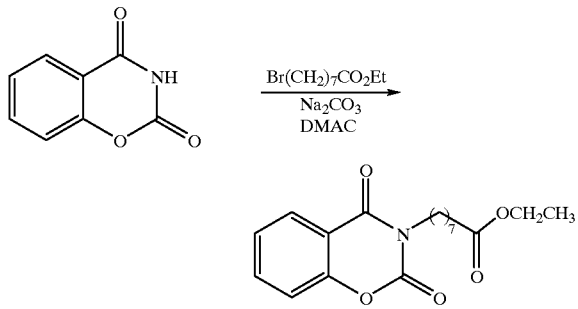

A 1 L, Pyrex glass, jacketed, bottom drain, laboratory reactor was used to perform this experiment. The temperature in the reactor was controlled with a circulating oil heat exchanger attached to the jacket on the reactor. This heat exchanger was capable of both cooling and heating. The reactor was equipped with an overhead turbine blade stirrer, temperature probe, and reflux condenser. The reactor was purged with nitrogen and the reaction was performed under an atmosphere of nitrogen. Dry N,N-dimethylacetamide (232 mL), 2H-1,3-benzoxazine-2,4(3H)-dione (62.0 g, 0.38 mol, 1.05 eq), and ethyl 8-bromo-octanoate (90.8 g, 0.36 mol, 1.0 eq) were charged to the reactor and the stirrer started. The reaction mixture was heated to about 70° C. over a 45 minute period. The reaction mixture was a nearly clear solution at this time. Sodium carbonate (45.0 g, 0.42 mol, 1.17 eq) was added in portions to the stirred reaction. There was some foaming during the initial part of the sodium carbonate addition. The reaction was held at about 70° C. for four hours after the sodium carbonate addition was complete. The reaction mixture temperature was lowered to approximately 40° C. The reaction mixture was drained into a sintered glass filter funnel and vacuum filtered into a 2 L side arm filter flask. The reactor was rinsed with ethanol (125 mL) and this rinse was used to wash the filter cake. The ethanol wash was allowed to combine with the previous reaction mixture filtrate. The filter flask was placed in an ice bath and the filtrate stirred magnetically. Deionized water (125 mL) was added to the stirred filtrate. The resulting slurry was stirred for 30 minutes while the ice bath remained in place. White solids were recovered by vacuum filtration through a sintered glass filter funnel. The filter cake was washed with heptane (155 mL). The cake was either used as is in the next step of the reaction sequence or was vacuum dried in a 40° C. oven for storage. The yield of ethyl 3-(8-octanoate)-2H-1,3-benzoxazine-2,4(3H)-dione was 90 to 95%.

EXAMPLE 10

Preparation of N-(2-hydroxybenzoyl)-8-amino)-octanoic Acid

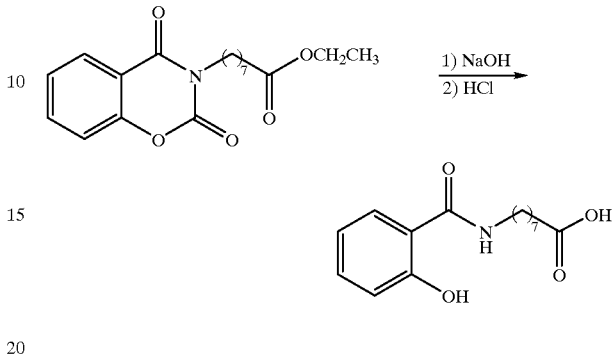

A 1 L stainless steel resin flask was set up with a stainless steel overhead turbine blade stirrer, stainless steel jacketed thermocouple thermometer, reflux condenser, and heating mantle. The reactor was charged with ethyl 3-(8-octanoate)-2H-1,3-benzoxazine-2,4(3H)-dione (200 g, 0.60 mol, 1.0 eq) and 20% (by weight) aqueous sodium hydroxide (480 g, 2.40 mol, 4.0 eq). The stirrer was started and the reaction slurry heated to about 98° C. over a 30 minute period. The reaction mixture was held at this temperature for one to two hours. The reaction mixture became a clear solution after the first hour at about 98° C.

A second reactor was set up with a three liter, round bottom, four neck flask. This reactor was equipped with a thermocouple thermometer, overhead stirrer, reflux condenser, ice bath cooling basin, and addition funnel. This reactor was charged with deionized water (330 mL), 37% (by weight) hydrochloric acid (215 g, 2.18 mol, 3.64 eq), and acetone (380 mL). The hydrolysis mixture in the stainless steel reactor was cooled to about 40° C. and transferred to the addition funnel on the second reactor. The stainless steel reactor was rinsed into the addition funnel with deionized water (110 mL). The hydrolysis mixture was added slowly with stirring to the hydrochloric acid solution. This addition was accompanied by the immediate precipitation of white solids in the acidification mixture. The addition rate was adjusted so that the foaming was controllable. The acidification reaction temperature was kept at approximately 45° C. with ice bath cooling. The pH of the acidification was adjusted to between 4.0 and 4.5 after the addition was complete by the incremental addition of concentrated hydrochloric acid. The ice bath was replaced with a heating mantle and the temperature of the acidified reaction mixture raised to about 65° C. and held at this temperature for 30 minutes. The solids in the acidification mixture formed an emulsion during this heat up. The reaction mixture was stirred and slowly cooled to ambient temperature giving a slurry. The solids in this slurry were recovered by vacuum filtration through a sintered glass fuel. The filter cake was washed with deionized water (440 mL). The wet cake was vacuum dried at about 50° C. overnight. The yield of N-(2-hydroxybenzoyl)-8-amino-octanoic acid was 85 to 95%.

EXAMPLE 11

Alternate Preparation of N-(2-hydroxybenzoyl)-8-aminiooctanoic Acid

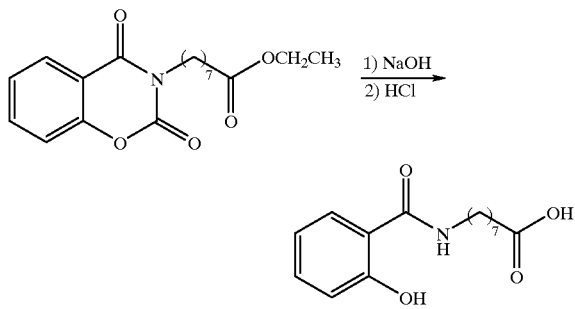

A 1 L stainless steel resin flask was set up with a stainless steel overhead turbine blade stirrer, stainless steel jacketed thermocouple thermometer, reflux condenser, and heating mantle. The reactor was charged with ethyl 3-(8-octanoate)-2H-1,3-benzoxazine-2,4(3H)-dione (200 g, 0.60 mol, 1.0 eq) and 20% (by weight) aqueous sodium hydroxide (480 g, 2.40 mol, 4.0 eq). The stirrer was started and the reaction slurry heated to about 98° C. over a 30 minute period. The reaction mixture was held at this temperature for one to two hours. The reaction mixture became a clear solution after the first hour at about 98° C.

A second reactor was set up with a three liter, round bottom, four neck flask. This reactor was equipped with a thermocouple thermometer, overhead stirrer, reflux condenser, water bath cooling basin, and addition funnel. The second reactor was charged with deionized water (333 mL), 37% (by weight) hydrochloric acid (230 g, 2.40 mol, 4.0 eq). The hydrolysis mixture in the stainless steel reactor was cooled to ambient temperature and transferred to the addition funnel on the second reactor. The hydrolysis mixture was added slowly with stirring to the hydrochloric acid solution. This addition was accompanied by the immediate precipitation of white solids in the acidification mixture. The addition rate was adjusted so that the foaming was controllable. This acidification is exothermic and the reaction temperature was allowed to rise to about 45° C. and kept at this temperature with occasional water bath cooling. The pH of the resulting slurry was adjusted with concentrated hydrochloric acid or 2N sodium hydroxide as needed to bring the final pH to between 4.0 and 4.5. The reaction mixture was then heated to about 65° C. and held at this temperature for 30 minutes. The reaction mixture was slowly cooled with stirring to ambient temperature. The solids in this slurry were recovered by vacuum filtration through a sintered glass funnel. The filter cake was washed with deionized water (230 mL). The wet cake was vacuum dried at about 50° C. overnight. The yield of N-(2-hydroxybenzoyl)-8-aminooctanoic acid was 85 to 95%.

EXAMPLE 12

Preparation of N-(2-hydroxy-5-chlorobenzoyl)-4-aminobutyric Acid 4-bromobutyric acid (26.17 g, 0.16 mol) was added to methanol (150 mL) and several drops sulfuric acid were added. This solution was refluxed for 3¼ hours. Thin layer chromatography (1:1 ethylacetate/hexane) was performed to determine the completion of ester formation. The solution was reduced in vacuo to an oil. The oil was dissolved in methylene chloride and washed with water, saturated sodium bicarbonate, and brine. The organic layer was dried over sodium sulfate and reduced in vacuo to yield 20.26 g of methyl(4-bromo)butanoate. The structure was confirmed by $^2$H NMR.

6-chlorocarsalam (12.4 g, 1.12 eq), methyl(4-bromo)butanoate (10.13 g, 1.0 eq), and 10.13 g sodium carbonate (10.13 g, 1.12 eq) were stirred in 50 mL dimethylacetamide (DMA). The solution was allowed to reflux for 4.5 hours, and then cooled to room temperature overnight. Solids were filtered off and washed with ethanol. Water and 2N sodium hydroxide was added to the filtrate. The mixture was heated for 2.5 hours. HPLC was performed showing completion of the hydrolysis. The solution was acidified with concentrated hydrochloric acid to a pH of about 1. The resulting white solid was filtered off, put over phosphorous pentaoxide ($P_2O_5$) in vacuo overnight. The solid was recrystallized in methanol/water, filtered and dried yielding 7.35 g of product. CHN calc. For $C_{11}H_{12}NO_4Cl$: C, 51.28; H, 4.69; N, 5.44: found: C, 50.92; H, 4.59; N, 5.46. Melting point 136–140° C.

EXAMPLE 13

Preparation of N-(5-chlorosalicyloyl)-8-aminocaprylic Acid

To a clean, dry, 200 gallon glass-lined reactor, 178 L of dry acetonitrile was added. The agitator was set to 100–125 rpm and the reactor contents were cooled to about 9° C. 74 kg of 5-chloro salicylamide, available from Polycarbon Industries of Leominster, Mass., was charged to the reactor and the charging port was closed. 47 L of dry pyridine was charged to the reactor. The resulting slurry was cooled to about 9° C. Cooling was applied to the reactor condenser and valve overheads were set for total reflux. Over 2 hours, 49.7 kg of ethylchlorofomate was charged to the 200 gallon reactor while maintaining the batch temperature at about 14° C. Note that ethylchloroformate can contain 0.1% phosgene and is extremely reactive with water. The reaction is highly exothermic and requires the use of a process chiller to moderate reaction temperature.

The reactor contents were agitated for 30 minutes at 10–14° C., once the ethylchloroformate addition was complete. The reactor contents were then heated to about 85° C. over 25 minutes, collecting all distillate into a receiver. The reactor contents were held at 85–94° C. for approximately 6 hours, collecting all distilled material into a receiver. The reaction mixture was sampled and the conversion (>90%) monitored by HPLC. The conversion was found to be 99.9% after 6 hours. The reactor contents were cooled to about 19° C. over a one-hour period. 134 L of deionized water was charged to the reactor. A precipitate formed immediately. The reactor contents were cooled to about 5° C. and agitated for 10.5 hours. The product continued to crystallize out of solution. The reactor slurry was centrifuged. 55 L of deionized water was charged to the 200-gallon, glass-lined reactor and the centrifuge wet cake was washed. The intermediate was dried under full vacuum (28" Hg) at 58° C. for 19.5 hours. The yield was 82.6 kg 6-chloro-2H-1,3-benzoxazine-2,4(3H)-dione This intermediate was packaged and stored so that it was not exposed to water.

In the next preparation, absolutely no water can be tolerated in the steps up to the point where distilled water is added.

222 L of dry dimethylacetamide was charged to a dry 200 gallon glass-lined reactor. The reactor agitator was set to 100–125 rpm. Cooling was applied to the condenser and valve reactor overheads were set for distillation. 41.6 kg of dry anhydrous sodium carbonate was charged to the reactor and the reactor charging port was closed. Caution was used due to some off-gassing and a slight exothermic reaction. 77.5 kg of dry 6-chloro-2H-1,3-benzoxazine-2,4(3H)-dione was charged to the reactor. Quickly, 88 kg of dry ethyl-8-bromooctanoate was charged to the reactor. The reaction was evacuated to 22–24 inches of vacuum and the reactor temperature was raised to 65–75° C. The reactor temperature was maintained and the contents were watched for foaming. The reactor mixture was sampled and monitored for conversion by monitoring for the disappearance of the bromo ester in the reaction mixture by gas chromatography. The reaction was complete (0.6% bromo ester was found) after 7 hours. The vacuum was broken and the reactor contents cooled to 45–50° C. The contents were centrifuged and the filtrate sent into a second 200 gallon glass-lined reactor. 119 L of ethanol (200 proof denatured with 0.5% toluene) was charged to the first 200 gallon reactor, wanned to about 45° C. and the filter cake washed with warm ethanol and this wash was charged to the reaction mixture in the second 200 gallon reactor.

The agitator was started on the second 200 gallon reactor. The reactor contents were cooled to about 29° C. 120 L distilled water was slowly charged to the second reactor, with the water failing directly into the batch. The reactor contents were cooled to about 8° C. The intermediate came out of solution and was held for 9.5 hours. The resultant slurry was centrifuged. 70 L ethanol was charged to the reactor, cooled to about 8° C., and the centrifuge cake was washed. The wet cake was unloaded into double polyethylene bags placed inside a paper lined drum. The yield was 123.5 kg of ethyl 8-(6-chloro-2H-1,3-benzoxazine-2,4(3H)-dionyl)octanoate.

400 L purified water, USP and 45.4 kg sodium hydroxide pellets were charged to a 200 gallon glass-lined reactor and the agitator was set to 100–125 rpm. 123.5 kg of the ethyl 8-(6-chloro-2H-1,3-benzoxazine-2,4(3H)-dionyl)octanoate wet cake was charged to the reactor. The charging port was closed. Cooling water applied to the condenser and the valve reactor overheads were set for atmospheric distillation. The reactor contents were heated to about 98° C. and the conversion was monitored by HLPC. Initially (approximately 40 minutes) the reactor refluxed at about 68° C., however, as the ethanol was removed (over 3 hours) by distillation the reactor temperature rose to about 98° C. The starting material disappeared, as determined by HPLC, at approximately 4 hours. The reactor contents were cooled to about 27° C. 150 L purified water, USP was charged to an adjacent 200 gallon glass-lined reactor and the agitator was set to 100–125 rpm. 104 L concentrated (12M) hydrochloric acid was charged to the reactor and cooled to about 24° C. The saponified reaction mixture was slowly charged (over 5 hours) to the 200 gallon glass-lined reactor. The material (45 L and 45 L) was split into 2 reactors (200 gallons each) because of carbon dioxide evolution. The product precipitated out of solution. The reaction mixture was adjusted to pH 2.0–4.0 with a 50% sodium hydroxide solution (2L water, 2 kg sodium hydroxide). The reactor contents were cooled to about 9–15° C. The intermediate crystallized out of solution over approximately 9 hours. The reactor slurry was centrifuged to isolate the intermediate. 50 L purified water, USP was charged to a 200 gallon glass-lined reactor and this rinse was used to wash the centrifuge wet cake. The wet cake was unloaded into double polyethylene bags placed inside a plastic drum. The N-(5-chlorosalicyloyl)-8-aminocaprylic acid was dried under vacuum (27" Hg) at 68° C. for 38 hours. The dry cake was unloaded into double polyethylene bags placed inside a 55-gallon, steel unlined, open-head drums with a desiccant bag placed on top. The dried isolated yield was 81 kg of N-(5-chilorosalicyloyl)-8-aminocaprylic acid.

All patents, patent applications, literature publications, and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A method of preparing an alkylated salicylamide from a protected/activated salicylamide, the method comprising the steps of (a) alkylating the protected/activated salicylamide with an alkylating agent to form a protected/activated alkylated salicylamide, and (b) deprotecting and deactivating the protected/activated alkylated salicylamide to form the alkylated salicylamide.

2. The method of claim 1, wherein the protected/activated salicylamide has the formula

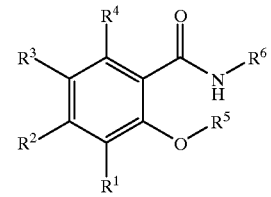

wherein $R^1$, $R^2$, $R^3$, and $R^4$ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)CH$_3$; —SO$_3$H; nitrile; or —NR$^9$R$^{10}$;

$R^9$ and $R^{10}$ are independently hydrogen, $C_1$–$C_4$ alkyl, or oxygen;

$R^5$ is a protecting group;

$R^6$ is an activating group; or $R^5$ and $R^6$ are combined to form a cyclic group.

3. The method of claim 2, wherein the protected/activated salicylamide has the formula

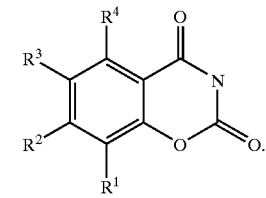

4. The method of claim 1, wherein the protected/activated salicylamide is prepared from a salicylamide having a hydroxy moiety and an amide moiety by
 (i) protecting the hydroxy moiety of the salicylamide; and
 (ii) activating the amide moiety of the salicylamide, simultaneously or in any order to form the protected/activated salicylamide.

5. The method of claim 4, wherein the protecting and activating steps are performed simultaneously.

6. The method of claim 4, wherein the protecting and activating steps are performed by reacting the salicylamide with an alkyl chloroformate.

7. The method of claim 6, wherein the alkyl chloroformate is ethyl chloroformate.

8. The method of claim 4, wherein the protecting and activating steps are performed by reacting the salicylamide with acetic anhydride.

9. The method of claim 1, wherein the alkylating step is performed for from about 3 to about 5 hours.

10. The method of claim 1, wherein the molar ratio of protected/activated salicylamide to alkylating agent is from about 1:0.8 to about 1:0.99.

11. The method of claim 1, wherein the alkylating step is performed in the presence of a base.

12. The method of claim 11, wherein the base is sodium carbonate.

13. The method of claim 1, wherein the alkylating step is performed at a temperature of from about 20 to about 100° C.

14. The method of claim 13, wherein the alkylating step is performed at a temperature of about 70° C.

15. The method of claim 1, wherein the alkylated salicylamide has the formula

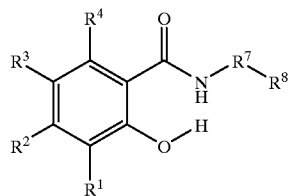

wherein $R^1$, $R^2$, $R^3$, and $R^4$ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)CH$_3$; —SO$_3$H; nitrile; or —NR$^9$R$^{10}$;

$R^9$ and $R^1$ are independently hydrogen, $C_1$–$C_4$ alkyl, or oxygen;

$R^7$ is a linear or branched, $C_1$–$C_{20}$ alkylene, alkenylene, or alkynylene;

$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteroaryl, or vinyl;

$R^7$ is optionally interrupted with aryl, heteroaryl, vinyl, oxygen, nitrogen, or sulfur; and $R^8$ is carboxyl or a salt thereof, carboxylate, nitrile, halogen, ester, amine or salt thereof, alcohol, or thiol.

16. The method of claim 1, wherein the alkylated salicylamide is N-(2-hydroxybenzoyl)-7-amino)heptanoic acid.

17. The method of claim 1, wherein the alkylated salicylamide is N-(2-hydroxybenzoyl)-8-amino)octanoic acid.

18. The method of claim 1, wherein the alkylated salicylamide is N-(2-hydroxybenzoyl)-10-amino)decanoic acid.

19. The method of claim 1, wherein the alkylated salicylamide is N-(2-hydroxy-5-chlorobenzoyl)-4-amino)butyric acid.

20. The method of claim 1, wherein the alkylated salicylamide is N-(2-hydroxy-5-chlorobenzoyl)-8-amino)octanoic acid.

* * * * *